United States Patent
Shaw et al.

(10) Patent No.: US 7,288,647 B2
(45) Date of Patent: Oct. 30, 2007

(54) RECOVERY OF CCI-779 FROM MOTHER LIQUORS

(75) Inventors: Chia-Cheng Shaw, St. Laurent (CA); Warren Chew, Outremont (CA); Bogdan Kazimierz Wilk, New City, NY (US); Genevieve Fortier, Ste-Foy (CA)

(73) Assignee: Wyeth, Madison, NJ (US)

( * ) Notice: Subject to any disclaimer, the term of this patent is extended or adjusted under 35 U.S.C. 154(b) by 115 days.

(21) Appl. No.: 11/359,842

(22) Filed: Feb. 22, 2006

(65) Prior Publication Data

US 2006/0199253 A1 Sep. 7, 2006

Related U.S. Application Data

(60) Provisional application No. 60/657,534, filed on Mar. 2, 2005.

(51) Int. Cl.
*C07D 498/18* (2006.01)

(52) U.S. Cl. .................................................... 540/456
(58) Field of Classification Search ............... 540/456
See application file for complete search history.

(56) References Cited

U.S. PATENT DOCUMENTS

| 3,993,749 | A | 11/1976 | Sehgal et al. |
| 5,362,718 | A | 11/1994 | Skotnicki et al. |
| 6,277,983 | B1 | 8/2001 | Shaw et al. |
| 2001/0039338 | A1 | 11/2001 | Shaw |
| 2005/0014777 | A1 | 1/2005 | Zhu |
| 2005/0033046 | A1 | 2/2005 | Chew et al. |

FOREIGN PATENT DOCUMENTS

| WO | WO-2005/010010 A1 | 2/2005 |
| WO | WO-2005/016935 | 2/2005 |

*Primary Examiner*—Bruck Kifle
(74) *Attorney, Agent, or Firm*—Arnold S. Milowsky; Howson & Howson LLP

(57) ABSTRACT

The invention provides a process for recovering CCI-779 from mother liquors.

15 Claims, No Drawings

RECOVERY OF CCI-779 FROM MOTHER LIQUORS

CROSS-REFERENCE TO RELATED APPLICATIONS

This application claims the benefit under 35 USC 119(e) of prior U.S. Provisional Patent Application No. 60/657,534, filed Mar. 2, 2005.

BACKGROUND OF THE INVENTION

This invention relates to the recovery of CCI-779 from mother liquors.

CCI-779 (rapamycin 42-ester with 3-hydroxy-2-(hydroxymethyl)-2-methylpropionic acid) is an ester of rapamycin, which has demonstrated significant inhibitory effects on tumor growth in both in vitro and in vivo models. CCI-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. CCI-779 has been demonstrated to be effective in multiple applications, including inhibition of central nervous system cancer, leukemia, breast cancer, prostate cancer, melanoma, gliomas, and glioblastoma.

The preparation and use of hydroxyesters of rapamycin, including CCI-779, is disclosed in U.S. Pat. No. 5,362,718. A regioselective synthesis of CCI-779 is described in U.S. Pat. No. 6,277,983. However, the yield of CCI-779 resulting is only in the range of 70-80%. Still another regioselective synthesis is described in US Patent Publication No. US 2005-0033046 A1. Recrystallization of CCI-779 is necessary in order to obtain crystalline product for use in clinical applications.

What is needed is a process for recovering additional crystalline CCI-779 from the mother liquors obtained as a by-product of CCI-779 crystallization.

SUMMARY OF THE INVENTION

The invention provides a process for the recovery of CCI-779 from mother liquors. The process includes concentrating the mother liquor, treating the concentrated CCI-779 with a buffer, drying and concentrating the organic layer, and recrystallizing the CCI-779, preferably from ether.

In another embodiment, the mother liquor obtained from the process is used in the process in order to obtain additional yields. In other embodiments, the process is repeated multiple times.

Other aspects and advantages of the invention will be apparent from the following detailed description of the invention.

DETAILED DESCRIPTION OF THE INVENTION

The present invention provides a novel method for the recovery of CCI-779 from mother liquors.

CCI-779 (rapamycin 42-ester with 3-hydroxy-2-(hydroxymethyl)-2-methylpropionic acid) can exist in the form of two isomers illustrated below in Scheme 2. The CCI-779 recovered from mother liquors in accordance with the invention generally contains about 95 wt % of CCI-779 Isomer B and about 3 wt % Isomer C.

As used herein, the terms combined yield or total combined yield mean the total CCI-779 recovered from all recrystallization steps, including initial recrystallization by conventional techniques and CCI-779 recovered from mother liquors by the process of the Invention.

In one embodiment, CCI-779 is prepared as described in U.S. Pat. No. 5,362,718. In another embodiment, CCI-779 is prepared as described in US Patent Publication No. US 2005-0033046 A1.

In another embodiment, CCI-779 is obtained from the acidic hydrolysis of rapamycin 42-ester with 2,2,5-trimethyl [1.3-dioxane]-5-carboxylic acid. In one embodiment this is accomplished using sulfuric acid followed by silica gel chromatography. The acidic hydrolysis is described in U.S. Pat. No. 6,277,983 (Shaw, et al.). Scheme 1 herein summarizes the hydrolysis process. Following hydrolysis, recrystallization is accomplished using conventional techniques. In one embodiment, recrystallization is performed with ether. Typically, the CCI-779 obtained from recrystallization has a B:C isomeric ratio in the range of about 30:1 to about 35:1, and a yield in the range of about 70% to about 80%, or about 72% to about 76%. In one embodiment, the CCI-779 obtained from recrystallization has a B:C isomeric ratio of about 32:1 and a yield of about 74%.

Scheme 1

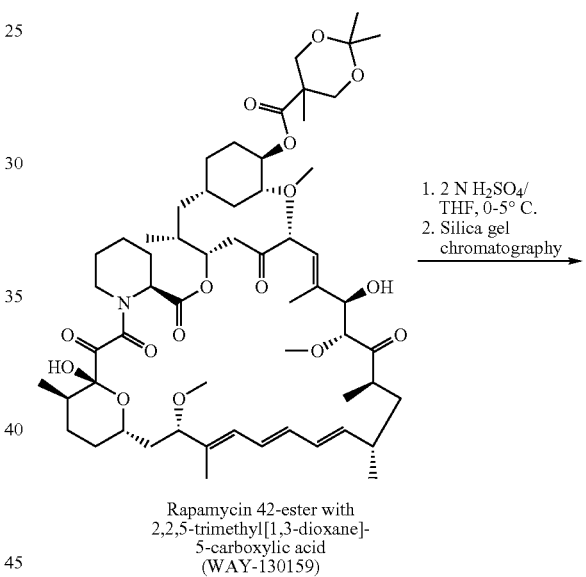

Rapamycin 42-ester with 2,2,5-trimethyl[1,3-dioxane]-5-carboxylic acid (WAY-130159)

1. 2 N $H_2SO_4$/ THF, 0-5° C.
2. Silica gel chromatography

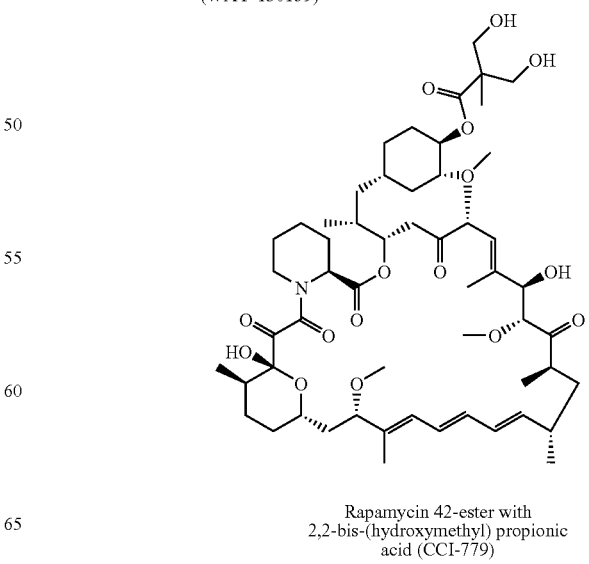

Rapamycin 42-ester with 2,2-bis-(hydroxymethyl) propionic acid (CCI-779)

The by-products of the recrystallization process are mother liquors containing additional CCI-779. Typically, the amount of CCI-779 present in the mother liquors is 20% or more of the product after recrystallization. In one embodiment, 25 to 26% of the CCI-779 product is present in the mother liquors. Further, the CCI-779 in these mother liquors contains a higher proportion of CCI-779 isomer C, i.e., a lower B:C ratio, than is typically found in CCI-779. In one embodiment, the B:C isomer ratio in the mother liquors is in the range of about 1.5:1 to 3:1, about 1.5:1 to 2.5:1, about 2:1 or about 1.6:1.

The presence of a greater percentage of isomer C in mother liquors, as opposed to that in the crystalline CCI-779, indicates a higher solubility of isomer C in the crystallization solvent. While not wishing to be bound by theory, isomer C is believed to be less crystalline than isomer B, leading to the increased presence of isomer C in the mother liquors. Applicants have discovered that the isomeric ratio can be increased in order to recover additional yield from mother liquors through modification of the pH. Scheme 2 herein illustrates the desired isomeric shift.

the organic solvent is tetrahydrofuran, acetonitrile, or acetic acid. In other embodiments, the solvent is a mixture of solvents, e.g., a mixture of acetone, tetrahydrofuran, acetonitrile, and/or acetic acid. In one embodiment, the volume ratio of solvent to buffer is between 1.5 to 1.1:1.0. In another embodiment, the volume ratio is 1.1:1.0. Other buffer systems, solutions, solvents, and volume ratios to adjust the pH are contemplated by the invention and would be known to one of skill in the art.

The solution of residual foam, from the mother liquors, and buffer system (i.e., buffer solution and solvent) is mixed. In one embodiment, the solution is mixed under nitrogen at a temperature of approximately 20 to 25° C. for 24 hours. In other embodiments, the solution is mixed for 48 hours. The length of time may be adjusted in order to maximize the ratio of isomer B to isomer C. In another embodiment, the ratio is monitored during the mixing, for example, by HPLC.

Following mixing, the product is separated by conventional means. In one embodiment, the mixture is diluted with ethyl acetate and washed with a brine solution. This is followed by washing of the organic layer (or organic layers

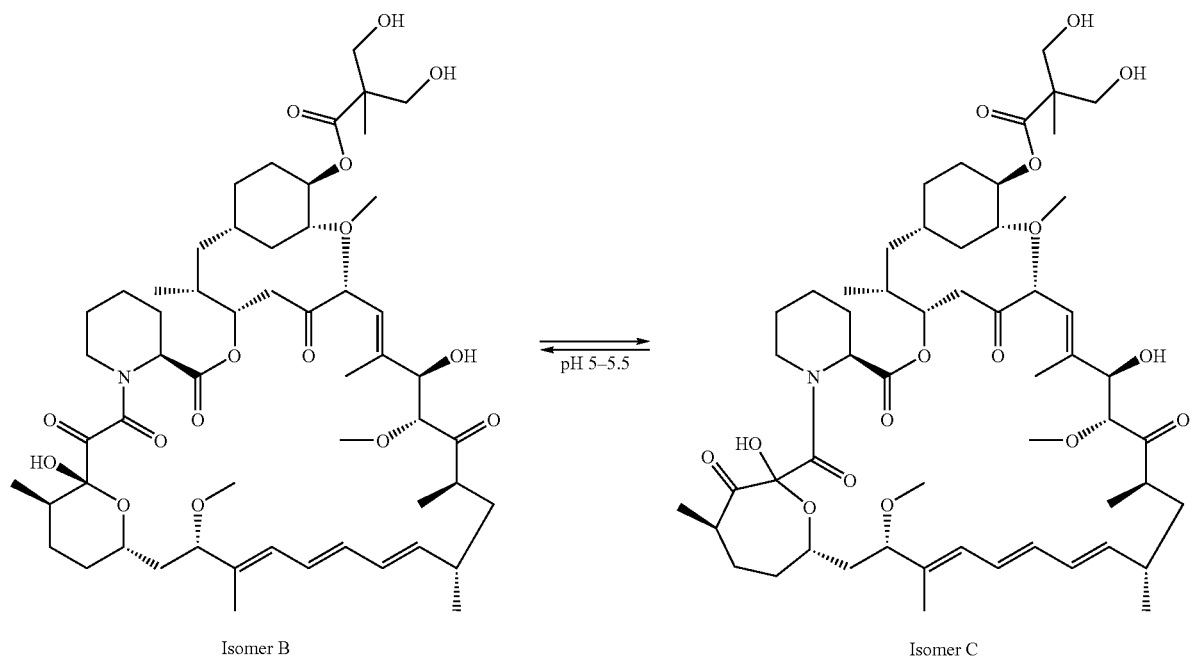

Scheme 2

Isomer B ⇌ (pH 5–5.5) Isomer C

Mother liquors obtained from the crystallization of CCI-779, as described above, are first concentrated under reduced pressure. The resulting foam is combined with a buffer system, i.e., a pH adjusting buffer (buffer solution) and solvent. In one embodiment, the pH of the buffer is approximately 5 to 6.5. In another embodiment, the pH of the buffer is approximately 5 to 5.5.

In one embodiment, the buffer solution contains sodium acetate. In other embodiments, the buffer solution contains potassium acetate or zinc acetate. In still other embodiments, the buffer solution contains a mixture or sodium acetate, potassium acetate, and/or zinc acetate. In one embodiment, the solvent is an organic solvent. In a further embodiment, the organic solvent is acetone. In still other embodiments, combined) with water and brine. The organic layer is then dried over sodium sulfate and concentrated under reduced pressure, generating a foam. Other methods of separating the product would be known to one of skill in the art, and are contemplated by the invention. The method of separating the product comprises addition of an organic medium so as to form the organic layer. Following separation, the foam is recrystallized by conventional techniques, e.g., precipitation. In one embodiment, the foam is recrystallized from an ether. In further embodiments, the ether is diethyl ether, or t-butyl methyl ether. As solvent for recrystallization there may also be used acetonitrile, a mixture of ether with hexanes or heptane, or a mixture of t-butyl methyl ether with hexanes or heptane. In still a further embodiment, the ether is diethyl ether. In one embodiment, the precipitated CCI-779 may be dried, for instance, under vacuum by conventional techniques.

In one embodiment, the recrystallized CCI-779 has a B:C isomer ratio greater than about 30:1. In other embodiments, the recrystallized CCI-779 has a B:C isomer ratio of about 45:1, or about 49:1, or greater. In still other embodiments, the recrystallized CCI-779 has a B:C isomer ratio of about 55:1, or about 57:1, or greater.

In other embodiments, the process is repeated using the mother liquors obtained from the process in order to obtain a desired total yield of CCI-779. In one embodiment, the total combined yield achieved by the process of the invention is about 90%, or about 95%, or greater. In other embodiment, the total combined yield achieved is about 98%, or greater. Scheme 3 below illustrates the process.

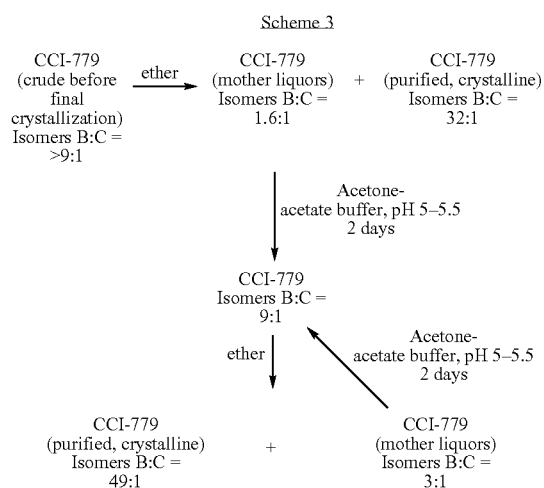

Scheme 3

The following example is illustrative of the present invention, but is not a limitation thereof.

EXAMPLE

Recovery of CCI-779 from Mother Liquors:

The acetate buffer (pH 5-5.5) was prepared by adding 400 ml of water to a suitable container followed by 5.5 g of sodium acetate and stirred to form a solution. To this solution was added 0.05 M acetic acid (300 ml) and stirred to form acetate buffer (pH 5-5.5). To a 2-L flask was charged 600 ml of acetone, followed by 545 ml of acetate buffer (pH 5-5.5). The mixture is stirred to form a homogeneous solution as 1.1:1 acetone-acetate buffer (pH 5-5.5).

To a 1-L flask was charged 500 g of CCI-779 mother liquor (diethyl ether solvent) (assay contained 7.9 % of CCI-779 with isomeric ratio B:C=1.6:1 ). The mother liquor was concentrated under reduced pressure to obtain 49.85 g of product as a foam. The foam was dissolved in 750 ml of 1.1:1 acetone-acetate buffer and mixed under nitrogen at 20 to 25° C. for a minimum of 24 h with the progress of the reaction monitored by HPLC. After one day, the ratio of B:C of a work-up sample was 8.1:1 and 9:1 after 48 h. The ratio of the two isomers remained the same after 48 h.

The reaction mixture was diluted with 1200 ml of ethyl acetate and washed with 300 ml of brine. The aqueous layer was separated and extracted with 300 ml of ethyl acetate. The organic layers were combined and washed with water (300 ml) and brine (300 ml). The organic layer was dried over sodium sulfate and then concentrated under reduced pressure to obtain 45.45 g of product as pale yellow foam. The foam was recrystallized from ether (180 ml). The product was dried in an vacuum oven at 50-55° C. to constant weight to obtain 22.5 g of product as a white crystalline solid with purity 93.2 % (isomer B+C) and an isomeric ratio of B:C=57:1. The recovery yield was 57%.

The mother liquor was concentrated under reduced pressure to obtain 19.5 g of product as a light yellow foam with B:C isomers ~3.3:1. The foam was treated with 300 ml of acetone-acetate buffer at 20 to 25° C. for 48 h. The reaction mixture was diluted with 450 ml of ethyl acetate and washed with 150 ml of brine. The aqueous layer was separated and extracted with 150 ml of ethyl acetate. The organic layers were combined, washed with water (200 ml), brine (200 ml), and dried over sodium sulfate. After concentration under reduced pressure, 17.24 g of product was obtained as light yellow foam with a B:C isomer ratio of 9:1. This material can be recrystallized from ether to obtain more crystalline CCI-779 as described in the process cycle.

All patents, publications, and other documents identified herein are incorporated by reference. One of skill in the art will recognize that minor modifications to the conditions and techniques described in the specific embodiments described herein can be varied without departing from the present invention. Such minor modifications and variants are within the scope of the invention as defined by the following claims.

The invention claimed is:

1. A process for recovering CCI-779 from mother liquors, comprising:
   (a) concentrating the mother liquor;
   (b) subjecting CCI-779 obtained by concentrating the mother liquor to treatment with a pH adjusting buffer having a pH in the range of about 5 to about 5.5;
   (c) subjecting the mixture to solvent extraction;
   (d) drying and concentrating the resultant organic layer; and
   (e) recrystallizing the CCI-779.

2. The process according to claim 1, wherein steps (a) through (d) are repeated using the mother liquor obtained from step (e).

3. The process according to claim 2, wherein the final combined yield exceeds 95%.

4. The process according to claim 2, wherein the final combined yield exceeds 98%.

5. The process according to claim 1, wherein the pH adjusting buffer comprises sodium acetate, potassium acetate, or zinc acetate.

6. The process according to claim 5, wherein the pH adjusting buffer comprises sodium acetate.

7. The process according to any claim 1, wherein the pH adjusting buffer is used with acetone, tetrahydrofuran, acetonitrile, or acetic acid as solvent.

8. The process according to claim 7, wherein the pH adjusting buffer is used with acetone as solvent.

9. The process according to claim 1, wherein an ether is used in recrystallization.

10. The process according to claim 1, wherein diethyl ether, t-butyl methyl ether, acetonitrile, a mixture of ether with hexanes or heptane, or a mixture of t-butyl methyl ether with hexanes or heptane is used as solvent for recrystallization.

11. The process according to claim 10, wherein the solvent is diethyl ether.

12. The process according to claim 1, further comprising the steps of:
(f) precipitating the CCI-779; and
(g) drying the CCI-779 under vacuum.

13. The process according to claim 1, wherein the CCI-779 produced thereby has a B:C isomeric ratio greater than 30:1.

14. The process according to claim 1, wherein the CCI-779 produced thereby has a B:C isomeric ratio greater than 45:1.

15. The process according to claim 1, wherein ethyl acetate is used as solvent for the solvent extraction.

* * * * *